US010620283B2

(12) United States Patent
Chantz

(10) Patent No.: US 10,620,283 B2
(45) Date of Patent: Apr. 14, 2020

(54) IMPLANTABLE OR INSERTABLE NUCLEAR MAGNETIC RESONANT IMAGING SYSTEM

(75) Inventor: Hyman D. Chantz, Scarsdale, NY (US)

(73) Assignee: International Business Machines Corporation, Armonk, NY (US)

(*) Notice: Subject to any disclaimer, the term of this patent is extended or adjusted under 35 U.S.C. 154(b) by 2325 days.

(21) Appl. No.: 13/469,681

(22) Filed: May 11, 2012

(65) Prior Publication Data
US 2012/0223708 A1 Sep. 6, 2012

Related U.S. Application Data

(62) Division of application No. 12/570,611, filed on Sep. 30, 2009, now Pat. No. 8,405,396.

(51) Int. Cl.
G01R 33/38 (2006.01)
G01R 33/58 (2006.01)

(52) U.S. Cl.
CPC ...... G01R 33/3808 (2013.01); G01R 33/3804 (2013.01); G01R 33/58 (2013.01)

(58) Field of Classification Search
CPC ............... G01R 33/46; G01R 33/3804; G01R 33/3808; G01R 33/58
USPC ........................................ 324/307, 309, 314
See application file for complete search history.

(56) References Cited

U.S. PATENT DOCUMENTS

| 4,672,972 A | 6/1987 | Berke |
| 4,923,459 A | 5/1990 | Nambu |
| 4,983,921 A | 1/1991 | Kramer et al. |
| 4,984,574 A * | 1/1991 | Goldberg et al. ............. 600/410 |
| 4,991,579 A | 2/1991 | Allen |
| 5,005,578 A | 4/1991 | Greer et al. |
| 5,572,132 A | 11/1996 | Pulyer et al. |
| 6,059,718 A | 5/2000 | Taniguchi et al. |
| 6,100,693 A | 8/2000 | Eberler et al. |
| 6,423,056 B1 | 7/2002 | Ishikawa et al. |

(Continued)

FOREIGN PATENT DOCUMENTS

WO WO2005067392 A2 7/2005

OTHER PUBLICATIONS

Office Action for U.S. Appl. No. 12/570,611 dated May 11, 2012.
(Continued)

Primary Examiner — Dixomara Vargas
(74) Attorney, Agent, or Firm — James Nock; Andrew M. Calderon; Roberts Mlotkowski Safran Cole & Calderon, P.C.

(57) ABSTRACT

Nuclear Magnetic Resonant Imaging (also called Magnetic Resonant Imaging or "MRI") devices which are implantable, internal or insertable are provided. The disclosure describes ways to miniaturize, simplify, calibrate, cool, and increase the utility of MRI systems for structural investigative purposes, and for biological investigation and potential treatment. It teaches use of target objects of fixed size, shape and position for calibration and comparison to obtain accurate images. It further teaches cooling of objects under test by electrically conductive leads or electrically isolated leads; varying the magnetic field of the probe to move chemicals or ferrous metallic objects within the subject. The invention also teaches comparison of objects using review of the frequency components of a received signal rather than by a pictorial representation.

9 Claims, 8 Drawing Sheets

(56) References Cited

U.S. PATENT DOCUMENTS

| | | | |
|---|---|---|---|
| 6,559,642 B2 | 5/2003 | King | |
| 6,862,468 B2 | 3/2005 | Smith | |
| 6,970,062 B2 | 11/2005 | Mulder | |
| 7,095,326 B2 * | 8/2006 | Young et al. | 340/572.4 |
| 7,277,807 B2 * | 10/2007 | Dieterle et al. | 702/76 |
| 7,368,912 B2 | 5/2008 | Kreibich | |
| 7,446,526 B2 | 11/2008 | Cunningham et al. | |
| 7,538,743 B1 | 5/2009 | Chantz | |
| 7,702,380 B1 | 4/2010 | Dean | |
| 8,433,421 B2 | 4/2013 | Atalar et al. | |
| 2006/0084861 A1 | 4/2006 | Blank et al. | |
| 2008/0039709 A1 | 2/2008 | Karmarkar | |

OTHER PUBLICATIONS

Bushberg et. al. "Magnetic Resonance Imaging (MRI)", The Essential Physics of Medical Imaging, Second Edition, 2002, Chapter 15, pp. 415-467, Cover page and Copyright page.

Haacke et al., "Introduction to MRI Coils and Magnets", Magnetic Resonance Imaging Physical Properties and Sequence Design, 1999, Chapter 27, pp. 827-859, Cover page and Copyright page.

Hummel, "Magnetic Properties of Materials—Applications", Electronic Properties of Materials, Third Edition, 2001, Chapter 17, pp. 349-364, Cover page and Copyright page.

Lide et al., "Nuclear Spins, Moments and Other Data Related to NMR Spectroscopy", CRC Handbook of Chemistry and Physics, 86th Edition, 2005, Section 9.92-9.94, Cover page and Copyright page.

Matter et al., "Three-Dimensional Prepolarized Magnetic Resonance Imaging Using Rapid Acquisition with Relaxation Enhancement", Magnetic Resonance in Medicine, vol. 56, Issue 5, 1085-1095, 2006.

Pines et al., "Magnetic Resonance Imaging with an Optical Atomic Magnetometer", Proceedings of the National Academy of Sciences of the United States of America, Aug. 22, 2006, vol. 103, No. 34, pp. 12668-12671.

Trushkin et al., "The Potential of a Noise-Reducing Antenna for Surface NMR Groundwater Surveys in The Earth's Magnetic Field", Geophysical Prospecting, Nov. 1994, vol. 42, No. 8, pp. 855-862.

"IVMRI Catheter, an "Inside-out" MRI, Filed with FDA", MedGadget LLC, Oct. 9, 2007, 3 pages.

Office Action dated Apr. 10, 2015 for related U.S. Appl. No. 13/469,671, 6 pages.

Notice of Allowance for related U.S. Appl. No. 12/570,611 dated Nov. 21, 2012.

Notice of Allowance dated Oct. 23, 2015 for related U.S. Appl. No. 13/469,671, 12 pages.

\* cited by examiner

IMPLANTABLE OR INSERTABLE NUCLEAR MAGNETIC RESONANT IMAGING SYSTEM

CROSS REFERENCE TO RELATED APPLICATIONS

The present application is a divisional application of copending application Ser. No. 12/570,611, filed on Sep. 30, 2009, the contents of which are incorporated by reference in their entirety herein.

FIELD OF THE INVENTION

The present invention generally relates to Nuclear Magnetic Resonant Imaging (also called Magnetic Resonant Imaging or MRI), and more particularly, to a method and apparatus for improving image generation, calibration, cost, efficiency, and associated techniques for Nuclear Magnetic Resonant Imaging.

BACKGROUND

MRI was founded on the notion that precise differentiation of nucleon precession frequencies was possible via magnetic gradients and Radio Frequency (RF) activity. The many device expositions of MRI, although formidable, are based on evolving engineering practices in signal processing and electromagnetic (EM) activity. Currently, a large macro-engineering MRI may give the best pictorial representation for most applications for the foreseeable future.

Briefly stated, the "classic" operation of a traditional MRI includes the following functionality:

A "significant" magnetic field aligns the electronic spins and some portion of the photonic hydrogen or other molecules in a patient;

Additional fields may have magnetic gradients in one or more axes;

Radio Frequency (RF) transmitter perturbs the spins of this previously-aligned field, in one or more times and uses a variety of gradient practices;

RF receiver records lifecycles of the perturbed spins; and

Processor collates computes and displayed the perturbed spin lifecycle, and translates them into a spectroscopic or image representation.

Most MRI devices have therefore been "outside in"; they are generally large objects wherein the subject under test is placed inside them. These "outside in" systems have traditionally been extremely large, heavy and expensive. Thus, they cannot be readily used in field or mobile diagnosis, nor can they be implanted or inserted in human or veterinary bodies.

A lesser number of MRI devices are "inside out"; they contain the magnetic and electrical probes which are insertable, internal and implantable in the subjects under test. Such subjects may range from large geological structures, to manmade objects, plants, animals, and humans. However, the current MRI devices that are "inside out" are prone to inaccuracy, overheating, and are expensive.

Accordingly, there exists a need in the art to overcome the deficiencies and limitations described hereinabove.

SUMMARY

In one aspect of the invention, a method is implemented for analyzing the structure and operations of an object under examination by magnetic resonant imaging, comprising the steps of: injecting, inserting or placing a plurality of reference object calibration targets of known size, geometric shapes, and magnetic profile, into or adjacent to an object under examination, at a plurality of locations; obtaining an image or radio frequency spectrum analysis of said object under examination by magnetic resonant imaging; and refining the image or radio frequency spectrum analysis obtained of such object under examination by enlarging or shrinking it in one or more linear dimensions, to conform to the characteristics of said reference object calibration targets.

In another aspect of the present invention, a method is provided for cooling an insertable, movable, or implantable MRI system comprising the steps of: inserting or moving an MRI device; cooling the inserted portion by use of an extrinsic cooling unit leads which remove heat from the inserted unit by thermal conduction, convection or radiation.

In yet another aspect of the present invention, a method is provided for conducting the comparative analysis of the structure and operations of an object under examination by magnetic resonant imaging, comprising comparing frequency-scans of the received signal without further processing of the signal to prepare a constructive image

BRIEF DESCRIPTION OF THE SEVERAL VIEWS OF THE DRAWINGS

The present invention is described in the detailed description which follows, in reference to the noted plurality of drawings by way of non-limiting examples of exemplary embodiments of the present invention.

DETAILED DESCRIPTION

Figure 1:
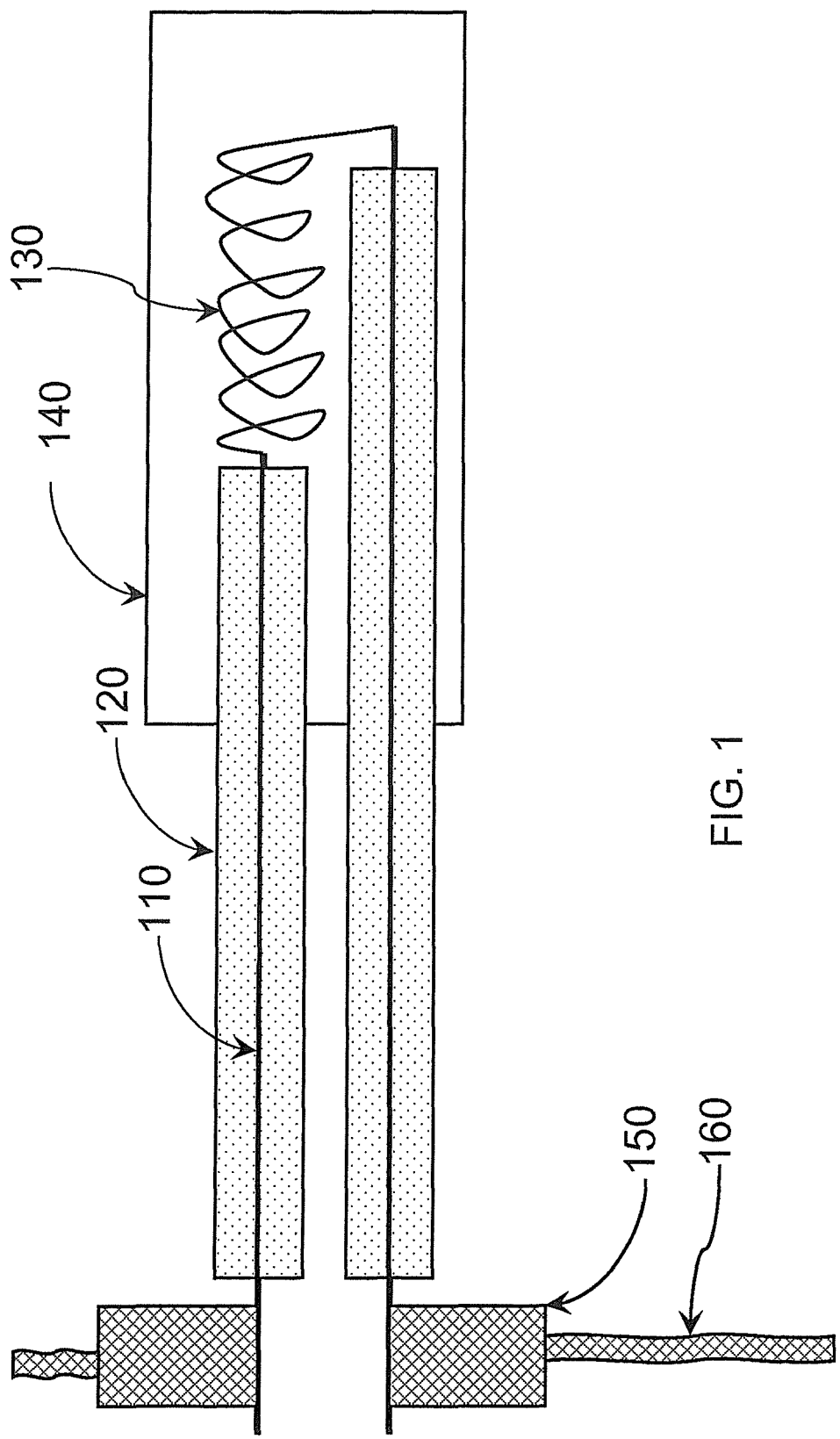
FIG. 1 shows an internal, implantatable or insertable MRI device with solid or stranded electrically-conducting cooling leads.

The present invention generally relates to Nuclear Magnetic Resonant Imaging (MRI), and more particularly, to a method and apparatus for improving image generation, calibration, cost, efficiency, and associated techniques for Nuclear Magnetic Resonant Imaging. More specifically, the invention improves an "inside-out" imaging device. The present invention can be used in a range of different applications such as, for example, diagnosis and monitoring of body functions, as discussed in more detail below.

In classical MRI, a large device has the luxury of an environment that has stability in many areas, including physical, environmental, shielding, electronic and magnetic. On the other hand, a miniature MRI may have advantages stemming from its small size. Its modest dimensions lend itself to internal stability. Thus, one can leverage the miniaturization to an advantage; and at least have rigidity in the implantation there. In addition, an implantable MRI has close—indeed direct—tissue contact. Therefore, although the Larmor frequency per-se requires high magnetic flux density, the RF needed to perturb the field may be smaller, and the received portion of the perturbed spins may be higher. Also, as the "leash" of MRI control cables can be very accurately designed and measured, it is possible to control phase very well. Further, although large high-Tesla magnets, both permanent and electro-resistive, require substantial infrastructure, miniaturized magnets in orthogonal dimensions can control a local magnetic field very well.

In embodiments, the present invention may use dynamic RF tailoring and tuning to compensate for difficulties in field congruity. In further embodiments, the present invention may use the same solenoid windings for DC magnetic field instantiation, both prime and gradient, as well as for AC RF generation and reception. Furthermore, the present invention may use analog scanning and spread-spectrum reception and transmission, to supplement or augment digital Fourier transform.

As will be appreciated by one skilled in the art, the present invention may take many forms of a "traveling" MRI in the object under test, such as, for example, similar to electronic lozenges used in endoscopy or colonoscopy. The present invention may also be assimilated with an insertable, implantable or internal MRI. The present invention may also use one or more injected, inert quality-control micro-targets for calibration. Additional embodiments are also provided for some potential usability in specific situations.

The present invention may use extremely small injectable, implantable, or attached ferrous spheres or other shapes as "targets" for system calibration. These can provide external readout of the magnetic shape, or can deform externally or internally by one-time or repeatable field use. In further embodiments, for an insertable or implanted MRI as described in the present invention, the MRI can be calibrated to aid in post-processing by active use of small injected or inserted micro targets, not only for calibration but whose possible evolution under certain chemical, thermal, or acoustic circumstances itself may be an indication of body function.

The present invention also can use low-cost signal processing by spectrum analyzer, as opposed to, or in conjunction with, transforming into pictorial representation. Also, embodiments of the present invention vary the magnetic field to push, infiltrate, and circulate magnetic therapeutic agents. Also, in embodiments, the present invention adjusts the cooling of the MRI device to conform to the magnetic activity.

In embodiments, the MRI need not be "on" continually, nor need it be totally internally self-contained. For example, the MRI of the present invention may conceptually be "on demand" or of specialized utility—e.g., tuned for spectroscopic analysis and differentiation of disease or healing products, in highly localized body areas. There are varying situations where a "constant" MRI may be useful, being on all or most of the time. But just as with a cardiac pacemaker, the full functionality of the MRI need not be always in use. It may be sufficient to have some vestigial or highly tuned functionality. In embodiments, the present invention may use external physical or inductive charging and tuning by patient or remote-via-modem to healthcare provider. Indeed, similar to ambulatory telemedicine, the present invention may take the form of a remote data collation suite where one expert healthcare provider monitors many implanted MRI. It is contemplated that implantation/insertion is for limited periods of time.

Not all components of the MRI need be co-located in the body. Accordingly, in embodiments, various components can be distributed internal and slightly sub-dermal, for example.

In the individual clinical situations, possible uses of an insertable or implanted MRI include brain and heart monitoring, and diabetes control and functionality. An MRI introduced under light sedation analogous to a colonoscopy or endoscope can be used for localized analysis of the efficacy of highly-potent infused drugs with magnetic markers. In embodiments, the MRI use of the present invention may occur by equipment logic or by the patient him/herself turning on the device during periods of perceived pain, etc.

MRI base functionality might further be used to slowly "leech" ferrous particles or drugs from a patient, or quickly use magnetic, as opposed to electric elements for cardiac rhythm renormalization. The MRI could be used, but in extreme situations, with pulsed MRI high magnetic fields used to deflect received ferrous metal munitions away from core body areas, as well as egress any shell fragments in a controlled matter. Although internal heating may otherwise be done by diathermy or other devices, this invention permits the infusion, dissemination or movement of chemicals by the same device which performs the analysis.

Although magnetic fields big and small may be difficult to directly control, RF fields are very amenable to control in frequency ($1 \times 10^{-9}$), phase, slew rate, and interference patterns. The MRI takes advantage of this by active electronics and continual tuning. In addition, in certain defined two dimensional circumstances, digital artifacts can be eliminated by a completely analog control unit.

Rather than pictorial representation, the present invention uses Fourier transform, or panoramic or spectrum analysis by an analog ramp generator and controlled phosphor persistence. This can be used for spectroscopic or low-resolution imaging, as well as for very accurate tuning of the local environment prior to FFT/DFT being established.

Magnetic Field Challenges—Generation

The central aspect of traditional MRI is proton spin and resonance. The Larmor resonant frequency can be described as. $\omega = \gamma B$. For protons, $\gamma$ equal 42.5775MHz/Tesla. Clearly, the resonant frequency is directly proportional to the frequency used: 1 Tesla 42.6 MHz, 10 Tesla 426 MHz, $1 \times 10^{-2}$ Tesla .42 MHz, etc. Thus, lower magnet strength would need a lower frequency.

The present invention can use known isotope or nucleon for efficiency. For example, Hydrogen 2H which is already among the highest in gyromagnetic ratio, can be implemented with the invention. Also, 3H which is slightly higher at 45.4158 MHz/Tesla can be used, but this has almost no abundance. Also, as to what is the strongest magnet which could be implanted or inserted, a threshold is the size of already-implanted types of devices, both one-time and free ranging. These known devices include, for example, cardiac pacemakers, insulin pumps, colonoscopy and endoscope devices, etc. Based on these devices, it is contemplated that 5 cm×2 cm device is appropriate. Also, the present invention proposes a "lozenge" shaped device with external power and control cabling. Using either Neodymium Iron Boride or Alnico D5, it is possible to obtain a small, local, permanent magnet for the main field of over 1 Tesla.

The present invention contemplates both permanent magnet and solenoid resistive electromagnets. Accordingly, although both permanent and resistive electromagnets are possible, for initial human use, it is contemplated that a permanent magnet for the main field be used and resistive electromagnets for the gradient field. It is contemplated, though, that a resistive electromagnetic for the initial field may be used after further testing.

As noted, a single loop of wire can produce a flux density of approximately:

$$B = \frac{\mu I a2}{2(a2 + (z-s)2)3/2}$$

Which can be reduced to the following for a solenoid:

$$B = \frac{\mu n I(\cos\alpha 1 - \cos\alpha 2)}{2}$$

In the above well-known equations, "B" is the magnetic field magnitude in Telis; "μ" is the relative permeability of the material in the core; n is the number of turns; "I" is the current through the wires in Amperes; "a" is the diameter of the solenoid; "z" is the long axis of the solenoid; "α1" is the angle of the wiring turn compared to the long axis "z"; and "α1" and "α2" are the angles from the long axis "z" to the diameters at the solenoid ends, from any point on the "z" axis.

An issue that may arise in an insertable MRI is the resistive heating $I^2R$ of the solenoid wire. Although the body's blood system continually carries away internal heat loads at a temperature of around 303° k, this is typically for a healthy individual. Although the present invention contemplates the use of a pulsed MRI to reduce heating, in a non-pulsed case it may be necessary to thermodynamically transfer significant energy from wire resistance, as well as from integral magnetic and RF tissue heating. As estimation, it may not be possible to countenance a net differential additional thermal load of more than 50 Joules, in this case 10 watts for five seconds. This would be distributed over the area of the lozenge, and if the heat dissipation was more-or-less uniform, no injury might be expected. In any event, it is contemplated that the MRI would include a thermostat to include rapid shutdown in an emergency.

Although tissue heating may be an issue, an electrical field magnet is contemplated for future implementation, particularly with a larger lozenge. It is also possible to include as necessary inward or in-and-out water cooling to the MRI "lozenge" and surrounding tissue. This could, for example, encompass calibrated flow, which could involve not only heat transfer and cooling, but metered velocity flow for imaging, or die or artifact introduction. The present invention also contemplates very tailored short field pulses, which although carrying the same or higher power (watts) would have less total energy (Joules) and could be thermally dissipated and mathematically analyzed quickly.

Even for the field solenoids, there are of course problems in hysteresis, eddy currents and core saturation. However, these may be addressed or compensated for as noted in the present disclosure. One embodiment of doing this is post-processing, by adjusting and stretching the raw image, to conform the image representation to calibration targets noted in the present disclosure. Also, the magnetic fields need not be perfect, or even homogenous. For incongruities can be resolved in post-processing, particularly if there is careful analog tuning and quality control calibration phantoms.

As an example, assume use of a 1.1 Tesla magnet, which provides an Larmor Frequency of around (1.1×42.6)=46.9 MHz for Hydrogen. (It is noted that 46.9 MHz is well within the US FCC Radio allocation of "Land Mobile" (30-50 MHz), for which outside transmitters are relatively few and low powered). Thus, it is unlikely that the typical MRI will effect or incur many problems. As the free speed of light is around 3×108 m/sec, $$\lambda = \frac{C}{f}$$

The resulting wavelength is about 6.2 meters, and a half wavelength for a dipole transmitter or receiver of about 3.1 meters.

However, the present invention does not need an antenna anywhere near this size. Instead, it is possible to use inductive coupling and conjugate matching to have a relatively efficient radiating and receiving element which is much smaller. Although this may have a very low radiation resistance, the present invention has a relatively small transmission line, and the overall efficiency is acceptable. Of course, this is all predicated on the fact that for MRI, a directional or steerable antenna per se is not needed; what is primarily needed is accurate frequency, phase and power control. Thus, MRI does not need a very large antenna capable of azimuthally correlation; rather, it is the presence of the wave itself with gives the spatial conformance. Of course, the smaller antenna may have lower input impedance, but the low frequency and short transmission line would ensure that little was actually lost.

For the purposes of this invention, a representative configuration will be a small insertable ovoid "lozenge" of approximately 5 cm×3 cm, which is connected via a small diameter cable to a power supply/controller unit (PSCU). The PSCU gives magnetic and RF power, and also is the RF receiver. In the PSCU are the control and readout capability.

Per-se FFT signal processing capability is not always required. Much of this can be done pre-processing in the frequency domain, by direct spectrum analysis or "panoramic" views by frequency sweeping. For example, on the output scope, the horizontal axis is the frequency expression; this is then swept by a saw tooth oscillator across the band. This may be swept say at 100 KHz, removing diminishing certain artifact situations.

By feeding AC and DC in various polarities, phases, series and differential ways, a thorough and subtle control of both RF and magnetic fields can be created. The device per-se would preferably have orthogonal elements, all fed through a narrow-diameter shielded cable to the control unit.

A configuration of the present invention may use a permanent magnet. In any event, gradients and RF transmitting and receiving control can be affected to support either a permanent field magnet, or an electromagnetically-derived field. Field uniformity is maintained and optional power and cooling can be provided. Of course, when the MRI lozenge is out of a patient, very high powered pulses might be used to reform the magnetic structure of the permanent magnet, to provide virtual "shim" tuning should that be necessary according to the industry practice known the ones skilled in the art.

FIG. 1 shows an internal, implantatable or insertable MRI device with solid or stranded electrically-conducting cooling leads in accordance with aspects of the invention. In embodiments, the electrically-conductive leads are thermally conductive to relieve the thermal load of the subject under test. For example, an electrical wire 110 of a material such as copper or other conductive material, which conducts both electricity and heat, is electrically shielded by a material such as polystyrene 120. In embodiments, the wire 110 is placed in an implantable, internal or insertable MRI device 140. Inside the MRI device 140 are a plurality of solenoid windings 130, which may be in a generally helix form. Although only one such winding, and one pair of wires, is depicted schematically for clarity, those of skill in the art will understand that the present invention contemplates more than one winding and more than one pair of wires. The windings 130 perform one or more functions of generating a magnetic field, varying the field, radio-frequency transmission and radio-frequency reception, for example. The heat generated with the insertable MRI device 140 may be deleterious to the object under test. For this reason, a non-electrically conductive, thermally-conductive cooled material such as ceramic 150 is in contact with or adjacent to one or more of the leads 110 to dissipate the heat, e.g., act as a heat sink. The ceramic or other cooling element 150 may itself be cooled by, convection, or radiation by an external liquid or solid heat drain 160, by Pettier cooling or by other mechanisms to remove heat from element 150.

Figure 2:
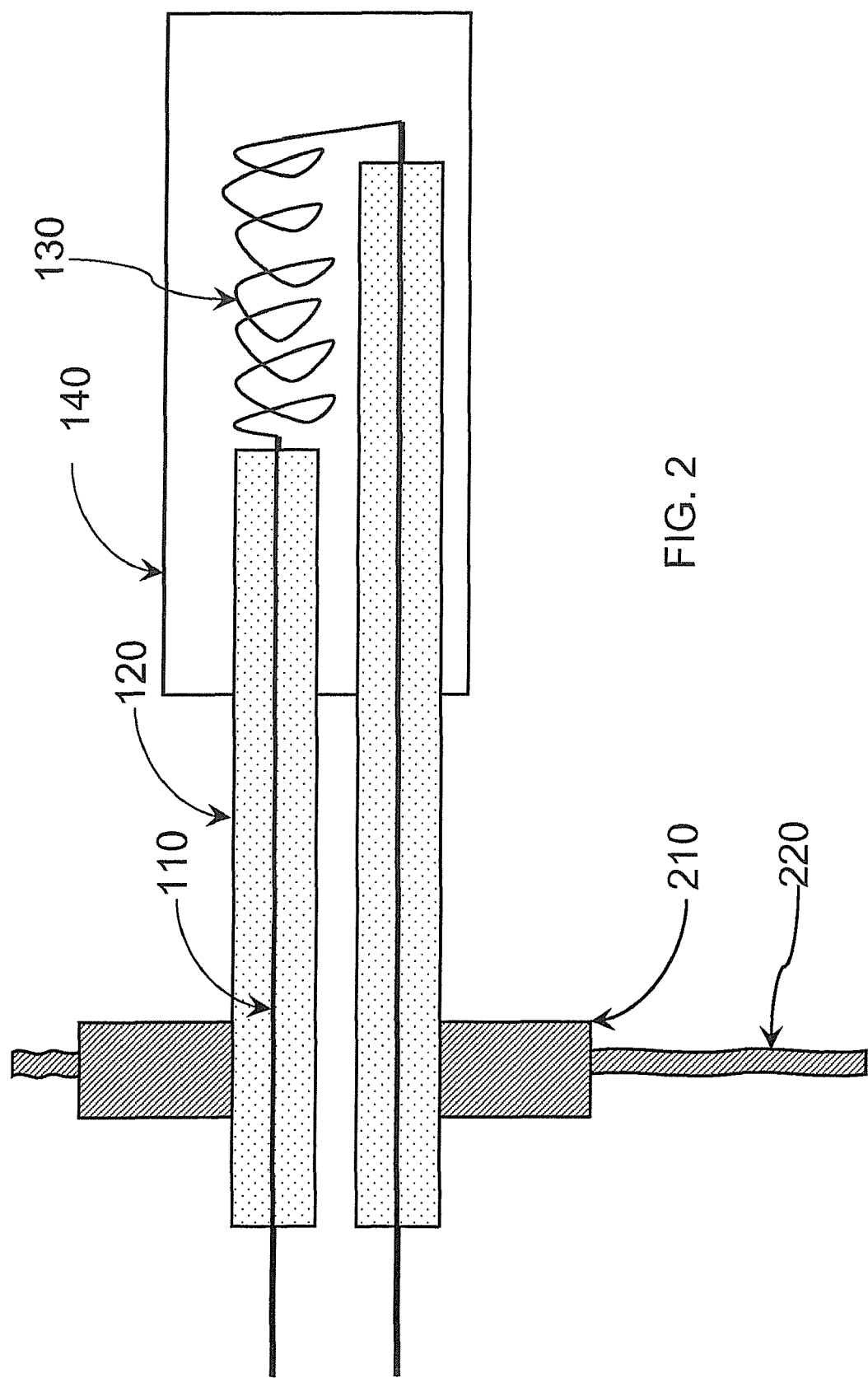
FIG. 2 shows an internal, implantatable or insertable MRI device with solid or stranded electrically-conducting cooling leads.

FIG. 2 shows an internal, implantable or insertable MRI device with solid or stranded electrically-conducting cooling leads in accordance with the invention. In embodiments of the invention, the electrical wiring 110 conducts electrical impulses to and from the inserted device, and the cooling is performed by a thermally conducting material 210 adjacent to the insulation 120 of the wiring 110, which is extrinsically cooled to remove thermal load at a position outside the device. In embodiments, the cooling element 210 is thermally conducting, and may or may not be electrically conducting. In other embodiments, the cooling element 210 is adjacent to the outer wire insulation 120 and attached to an external liquid or solid heat drain 220.

Figure 3:
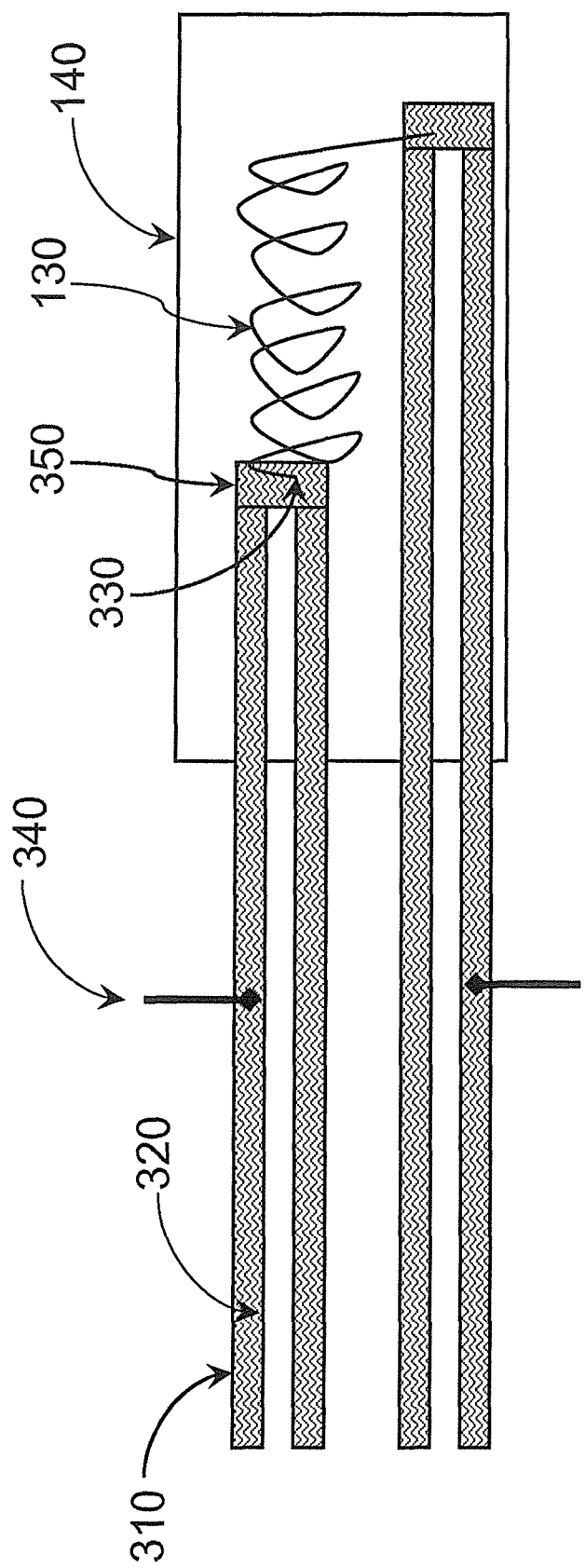
FIG. 3 shows an internal, insertable or implantable MRI device with liquid, electrically conductive cooling leads.

FIG. 3 shows an internal, insertable or implantable MRI device with liquid, electrically conductive cooling leads in accordance with aspects of the invention. In embodiments, the liquid carries the electric currents to the magnet and in addition is thermally conductive to relieve the thermal load of the subject under test. In embodiments, flexible, electrically insulated tubing 310 made of a material such as plastic is filled with a circulating, electrically-conductive liquid 320 such as a saline solution in water. The electrically-conductive liquid 320 is circulated through a heat-exchanger 350 within the MRI device 350. In FIG. 3 as shown, there are two pairs of tubing, with the upper pair electrically isolated from the lower pair. An external electrode 340 introduces current for magnetic or radio-frequency MRI use, and this is carried by the respective electrically-conductive liquid 320 to an internal MRI electrode 330 which powers the MRI solenoid 130.

Figure 4:
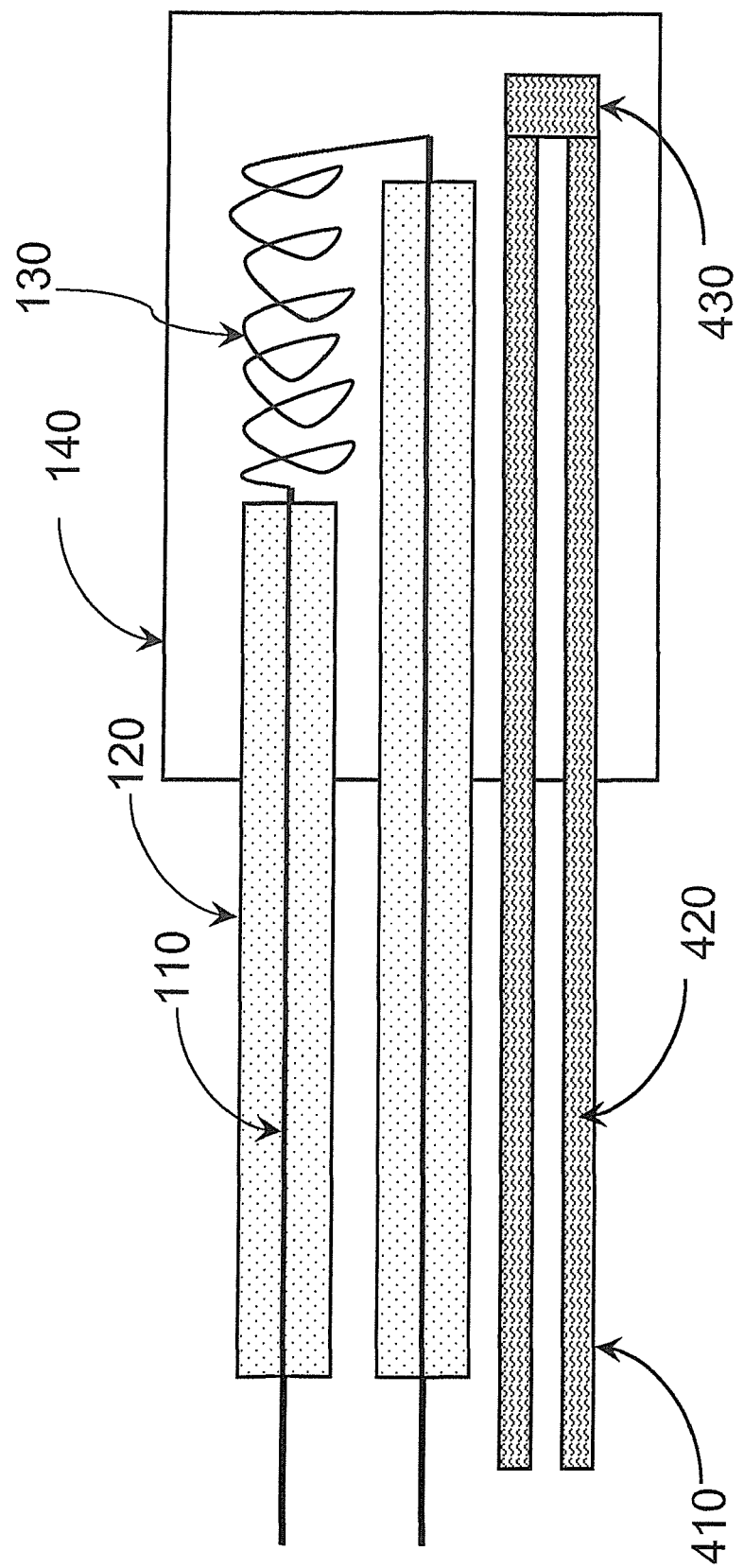
FIG. 4 shows an internal, insertable or implantable MRI device with liquid conductive cooling.

FIG. 4 shows an internal, insertable or implantable MRI device with liquid conductive cooling, where the liquid does not provide electrical current capability, but is thermally conductive to relieve the thermal load of the subject under test. In embodiments, a flexible, electrically insulated tubing 410 made of a material such as plastic is filled with a circulating liquid 420 such as a saline solution in water. The saline solution 420 flows to a heat-exchanger cooling head 430 within the MRI device 140.

Figure 5:
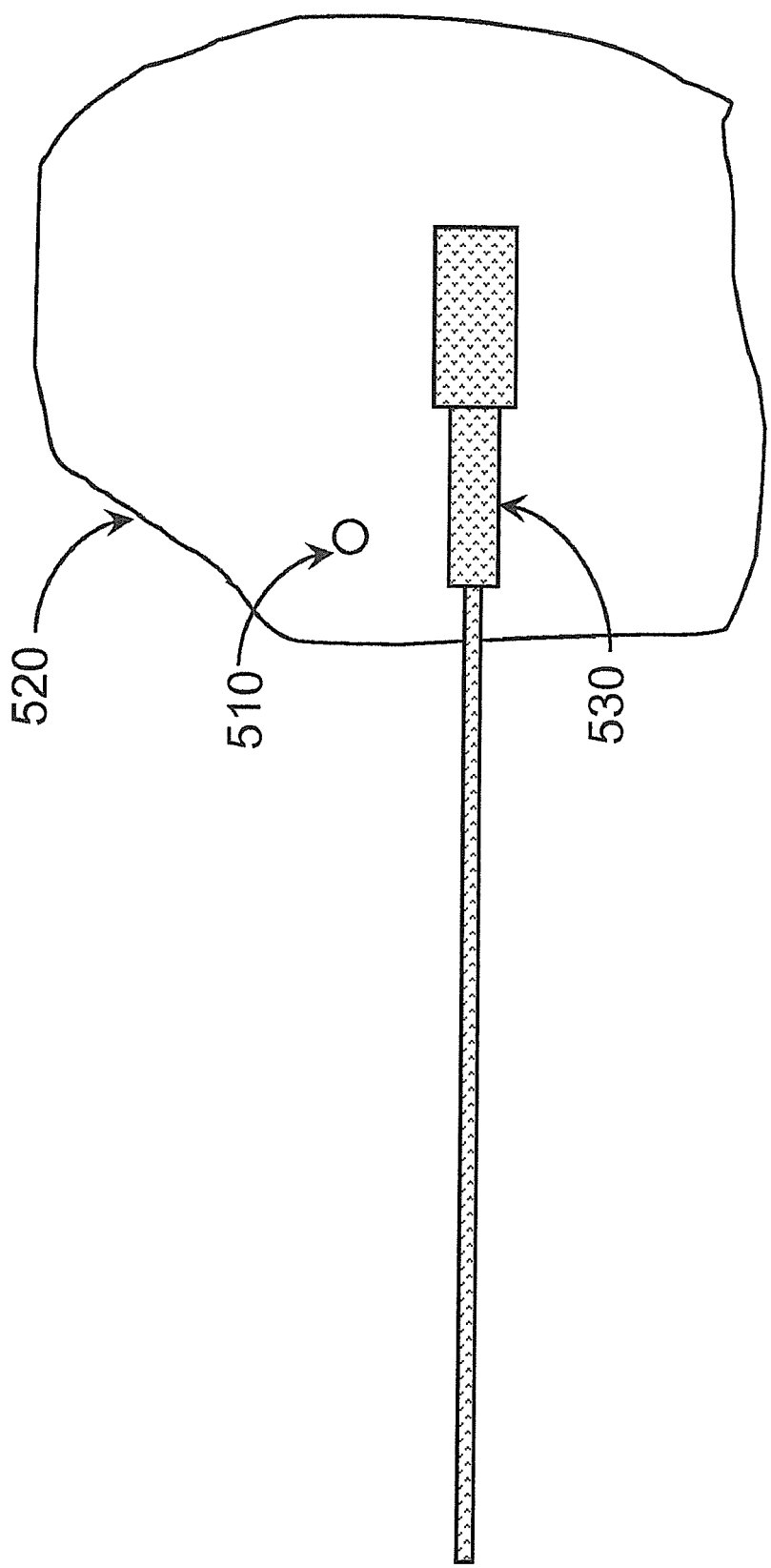
FIG. 5 shows an inserted geometric calibration object which is used for calibration of the radio-frequency received images.

FIG. 5 shows an inserted geometric calibration object which is used for calibration of the radio-frequency received images in accordance with the invention. In this embodiment, one or more objects of known geometric size and shape 510 are inserted, injected, or implanted in the object under test 520 to serve as references for pictorial representation by the MRI device. 530. Although many shapes are contemplated by the invention, spherical shapes objects provide the same ideal shape under any angle or orientation of viewing. The targets may be inert, and/or bio-absorbable.

Figure 6:
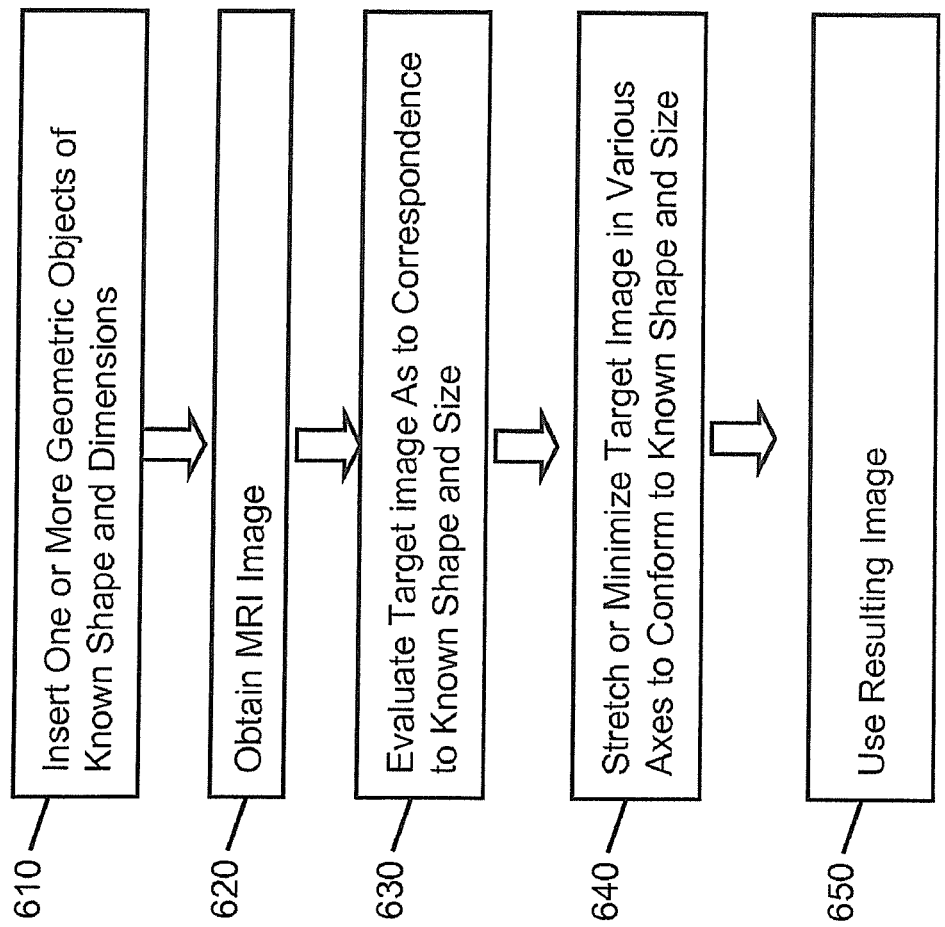
FIG. 6 shows a method of calibrating the visible image to one or more inserted calibration targets.

FIG. 6 shows a method of calibrating the visible image to one or more inserted calibration targets. At step 610, the present invention inserts one or more geometric objects of known shape and size (e.g., dimension). For example, this can be one spherical target using a spherical target, on an X/Y axis viewer. At step 620, the present invention obtains an MRI image. At step 630, the target image is evaluated as to correspondence to known shape and size. At step 640, the present invention stretches or minimizes target image in various axes to conform to known shape and size using a spherical target, on an X/Y axis viewer. In other embodiments, optical or electronic image techniques can be used to stretch the image. This image may be stretched optically by lenses, electronically by a computer display using commonly-available image processing software, or other means. After the image is stretched to conform to targets of known shape and size, it produces more accurate representation of the image. At step 650, the present invention uses the resulting image.

Figure 7:
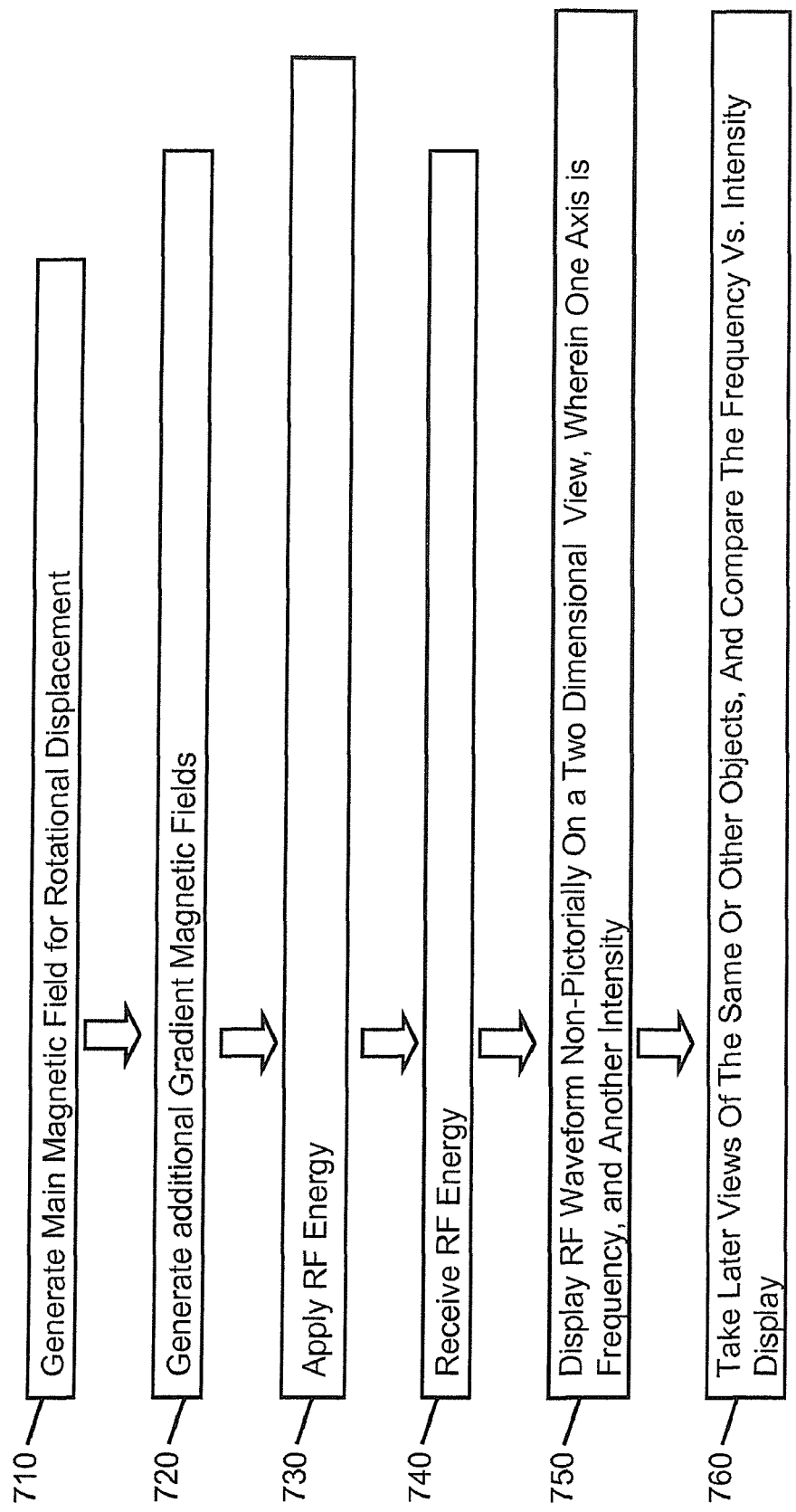
FIG. 7 shows an internal, insertable or implantable MRI device where comparisons of the object-under-test are made by radio-frequency spectrums analysis.

FIG. 7 shows an internal, insertable or implantable MRI device where comparisons of the object-under-test are made by radio-frequency spectrums analysis, not pictorial representation per-se. In this example, the traditional MRI proton 'knock down and recover' sequences are performed in a conventional manner. At step 710, the present invention generates main magnetic field for rotational displacement. At step 720, the present invention generates additional gradient magnetic fields. At step 730, the present invention applies RF energy to the objects under examination. At step 740, the present invention receives RF energy. In this implementation, the present invention bypasses a pictorial representation and performs the processes of step 750. In particular, at step 750, the present invention displays RF waveform non-pictorially on a two dimensional view, wherein one axis is frequency, and another intensity. At step 760, the present invention will take later views of the same or other objects, and compare the frequency vs. intensity display of the received RF energy. The advantages of not proceeding to a pictorial display are that the MRI equipment is much cheaper, and the receiver element can use simple saw tooth generators for frequency sweep. Although no pictorial representation is used, the differential between two images can be discerned by this depiction.

Figure 8:
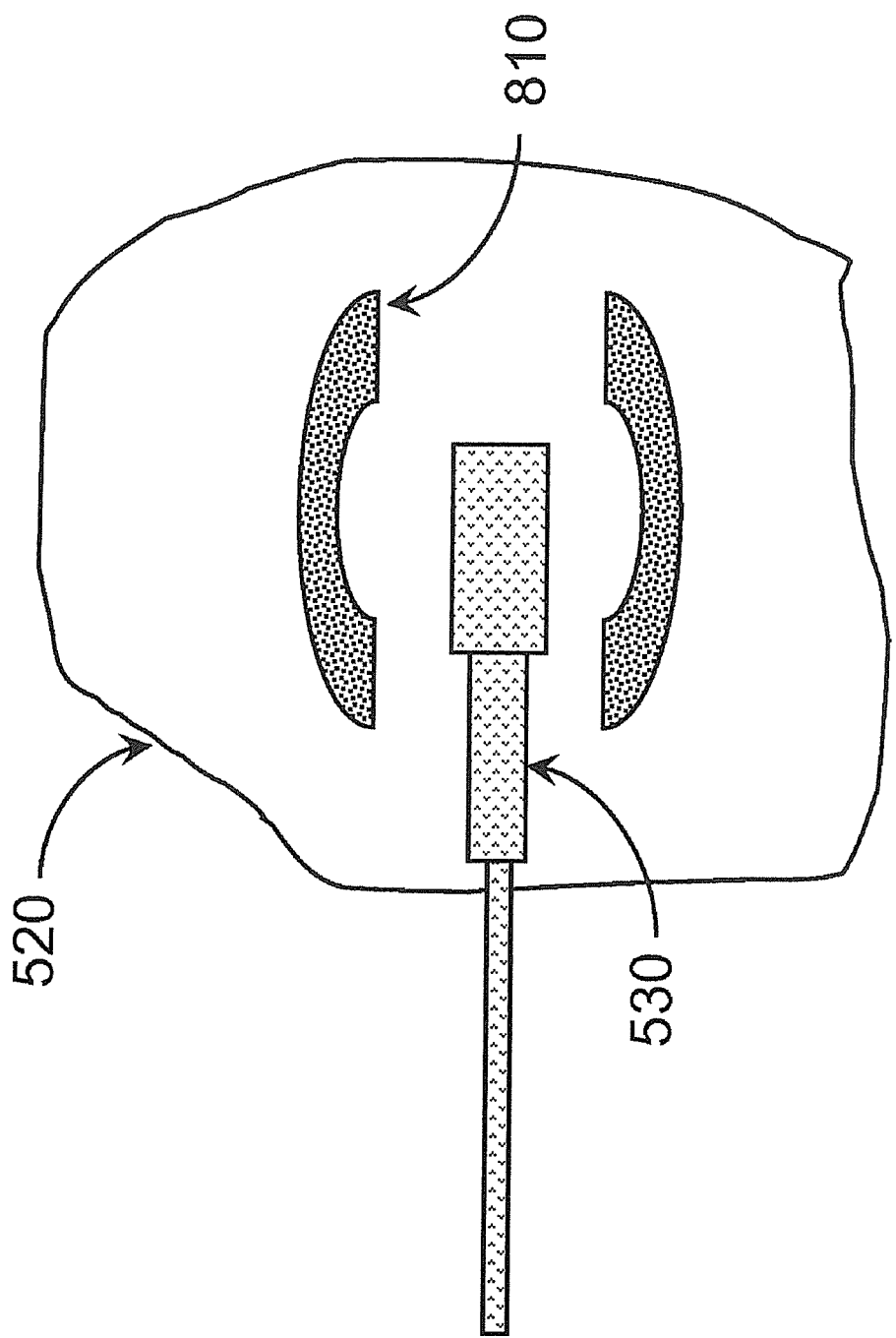
FIG. 8 shows infusion, migration, diffusion or leaching of magnetic-relevant chemical elements, or solid ferrous objects.

FIG. 8 shows infusion, migration, diffusion or leaching of magnetic-relevant chemical elements or solid ferrous objects by varying the magnetic field of the internal, insertable or implantable MRI device in accordance with aspects of the invention. For example, magnetically susceptible and/or magnetically charged solutions or particles 810 are injected into the object under test 520. These particles 810 may be diffused throughout the object under test 520 by the magnetic elements in the MRI device 530. As the object-under-test's thermal load may be particularly high, embodiments of the present invention contemplate performing this with a cooled MRI device, using one of the cooling techniques previously described.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims, if applicable, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principals of the invention and the practical application, and to enable others of ordinary skill in the art to understand the invention for various embodiments with various modifications as are suited to the particular use contemplated. Accordingly, while the invention has been described in terms of embodiments, those of skill in the art will recognize that the invention can be practiced with modifications and in the spirit and scope of the appended claims.

What is claimed:

1. A method for conducting a comparative analysis of the structure and operations of an object under examination by magnetic resonant imaging, comprising comparing frequency scans of a received signal without further processing of the signal to prepare a constructive image.

2. The method of claim 1, wherein the frequency scans of the received signal is performed by a panoramic receiver.

3. The method of claim 1, wherein the frequency scans of the received signal is performed by Fast Fourier Transform Analysis of a received waveform.

4. The method of claim 1, wherein the frequency scans of the received signal is performed by a tracking receiver tuned by a ramp generator.

5. The method of claim 1, wherein the method bypasses pictorial representation, and uses Fourier transform, or panoramic or spectrum analysis by an analog ramp generator and controlled phosphor persistence.

6. The method of claim 4, wherein the ramp generator is an analog ramp generator.

7. The method of claim 6, further comprising frequency sweeping by a saw tooth oscillator across a frequency band.

8. The method of claim 7, wherein the frequency sweeping occurs at 100 KHz to remove artifact situations.

9. The method of claim 8, wherein the frequency scans are displayed in a two-dimensional view such that one axis of the two-dimensional view is frequency and another axis of the two-dimensional view is intensity.

* * * * *